(12) United States Patent
Nguyen et al.

(10) Patent No.: US 10,668,251 B2
(45) Date of Patent: Jun. 2, 2020

(54) DEFLECTABLE VARIABLE RADIUS CATHETERS

(71) Applicant: St. Jude Medical, Atrial Fibrillation Division, Inc., St. Paul, MN (US)

(72) Inventors: Duy Nguyen, Corona, CA (US);
Sheldon Nelson, Plymouth, MN (US);
Elizabeth Nee, Minneapolis, MN (US);
Guy P. Vanney, Blaine, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 16/031,494

(22) Filed: Jul. 10, 2018

(65) Prior Publication Data
US 2019/0015634 A1 Jan. 17, 2019

Related U.S. Application Data

(60) Continuation of application No. 13/430,428, filed on Mar. 26, 2012, now Pat. No. 10,052,457, which is a division of application No. 12/569,786, filed on Sep. 29, 2009, now Pat. No. 8,182,467, which is a division of application No. 11/647,311, filed on Dec. 29, 2006, now abandoned.

(60) Provisional application No. 60/800,851, filed on May 17, 2006.

(51) Int. Cl.
*A61M 25/01* (2006.01)
*A61M 25/00* (2006.01)
*A61M 25/10* (2013.01)

(52) U.S. Cl.
CPC .... *A61M 25/0152* (2013.01); *A61M 25/0043* (2013.01); *A61M 25/0136* (2013.01); *A61M 25/0141* (2013.01); *A61M 25/0147* (2013.01); *A61M 2025/015* (2013.01); *A61M 2025/0161* (2013.01); *A61M 2025/105* (2013.01)

(58) Field of Classification Search
CPC .......... A61M 25/0152; A61M 25/0141; A61M 25/0136; A61M 25/0147; A61M 2025/0161
See application file for complete search history.

(56) References Cited

U.S. PATENT DOCUMENTS

| | | | |
|---|---|---|---|
| 5,318,525 | A | 6/1994 | West et al. |
| 5,354,297 | A | 10/1994 | Avitall |
| 5,368,564 | A | 11/1994 | Savage |
| 5,391,147 | A | 2/1995 | Imran et al. |
| 5,397,304 | A | 3/1995 | Truckai |
| 5,431,168 | A | 7/1995 | Webster, Jr. |
| 5,472,017 | A | 12/1995 | Kovalcheck |
| 5,478,330 | A | 12/1995 | Imran et al. |
| 5,562,619 | A | 10/1996 | Mirarchi et al. |

(Continued)

*Primary Examiner* — Sean P Dougherty
(74) *Attorney, Agent, or Firm* — Wiley Rein LLP

(57) ABSTRACT

The invention provides a deflectable catheter capable of forming many variable radius spiral forms from a single, flexible, distal end section. In one aspect, the catheter employs a variable radius control wire to extend or deform a pre-formed loop structure into a three dimensional spiral-like form or geometry. The ability of a single catheter to create a multitude of shapes and sizes allows users to access to a number of anatomical areas without changing the catheter during a procedure or treatment. In another aspect, the invention encompasses methods of producing deflectable variable radius catheters, where two or more regions of the catheter having common control wires are fused or formed onto one another.

17 Claims, 12 Drawing Sheets

(56) References Cited

U.S. PATENT DOCUMENTS

| | | |
|---|---|---|
| 5,588,964 A | 12/1996 | Imran et al. |
| 5,611,777 A | 3/1997 | Bowden et al. |
| 5,656,029 A | 8/1997 | Imran et al. |
| 5,755,760 A | 5/1998 | Maguire et al. |
| 5,772,641 A | 6/1998 | Wilson |
| 5,820,591 A | 10/1998 | Thompson et al. |
| 5,827,278 A | 10/1998 | Webster, Jr. |
| 5,836,947 A | 11/1998 | Fleischman et al. |
| 5,865,800 A | 2/1999 | Mirachi et al. |
| 5,885,278 A | 3/1999 | Fleischman |
| 5,897,529 A | 4/1999 | Ponzi |
| 5,910,129 A | 6/1999 | Koblish et al. |
| 5,916,213 A | 6/1999 | Haissaguerre et al. |
| 5,935,124 A | 8/1999 | Klumb et al. |
| 5,971,983 A | 10/1999 | Lesh |
| 5,984,917 A | 11/1999 | Fleischman et al. |
| 6,002,955 A | 12/1999 | Willems et al. |
| 6,004,269 A | 12/1999 | Crowley et al. |
| 6,023,638 A | 2/2000 | Swanson |
| 6,024,740 A | 2/2000 | Lesh et al. |
| 6,027,473 A | 2/2000 | Ponzi |
| 6,048,329 A | 4/2000 | Thompson et al. |
| 6,064,905 A | 5/2000 | Webster et al. |
| 6,066,125 A | 5/2000 | Webster, Jr. |
| 6,068,629 A | 5/2000 | Haissaguerre et al. |
| 6,071,274 A | 6/2000 | Thompson et al. |
| 6,071,279 A | 6/2000 | Whayne et al. |
| 6,071,282 A | 6/2000 | Fleischman |
| 6,076,012 A | 6/2000 | Swanson et al. |
| 6,080,151 A | 6/2000 | Swartz et al. |
| 6,083,222 A | 7/2000 | Klein et al. |
| 6,090,104 A | 7/2000 | Webster, Jr. |
| 6,117,101 A | 9/2000 | Diederich et al. |
| 6,120,476 A | 9/2000 | Fung et al. |
| 6,123,699 A | 9/2000 | Webster, Jr. |
| 6,164,283 A | 12/2000 | Lesh |
| 6,171,277 B1 | 1/2001 | Ponzi |
| 6,198,974 B1 | 3/2001 | Webster, Jr. |
| 6,203,525 B1 | 3/2001 | Whayne et al. |
| 6,210,362 B1 | 4/2001 | Ponzi |
| 6,210,407 B1 | 4/2001 | Webster |
| 6,212,426 B1 | 4/2001 | Swanson |
| 6,214,002 B1 | 4/2001 | Fleischman |
| 6,221,070 B1 | 4/2001 | Tu et al. |
| 6,224,587 B1 | 5/2001 | Gibson |
| 6,245,064 B1 | 6/2001 | Lesh et al. |
| 6,254,599 B1 | 7/2001 | Lesh et al. |
| 6,264,654 B1 | 7/2001 | Swartz et al. |
| 6,302,875 B1 | 10/2001 | Makower et al. |
| 6,305,378 B1 | 10/2001 | Lesh |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,330,473 B1 | 12/2001 | Swanson et al. |
| 6,356,790 B1 | 3/2002 | Maguire et al. |
| 6,371,955 B1 | 4/2002 | Fuimano et al. |
| 6,383,151 B1 | 5/2002 | Diederich et al. |
| 6,402,746 B1 | 6/2002 | Whayne et al. |
| 6,416,511 B1 | 7/2002 | Lesh et al. |
| 6,454,758 B1 | 9/2002 | Thompson et al. |
| 6,500,167 B1 | 12/2002 | Webster, Jr. |
| 6,542,781 B1 | 4/2003 | Koblish et al. |
| 6,544,262 B2 | 4/2003 | Fleischman |
| 6,554,794 B1 | 4/2003 | Mueller et al. |
| 6,582,536 B2 | 6/2003 | Shimada |
| 6,599,288 B2 | 7/2003 | Maguire et al. |
| 6,602,278 B1 | 8/2003 | Thompson et al. |
| 6,605,087 B2 | 8/2003 | Swartz et al. |
| 6,628,976 B1 | 9/2003 | Fuimaono et al. |
| 6,645,202 B1 | 11/2003 | Pless et al. |
| 6,689,128 B2 | 2/2004 | Sliwa et al. |
| 6,701,931 B2 | 3/2004 | Sliwa et al. |
| 6,702,811 B2 | 3/2004 | Stewart et al. |
| 6,711,428 B2 | 3/2004 | Fuimaono et al. |
| 6,719,755 B2 | 4/2004 | Sliwa, Jr. et al. |
| 6,743,227 B2 | 6/2004 | Seraj et al. |
| 6,745,080 B2 | 6/2004 | Koblish |
| 6,752,805 B2 | 6/2004 | Maguire et al. |
| 6,771,996 B2 | 8/2004 | Bowe et al. |
| 6,795,721 B2 | 9/2004 | Coleman et al. |
| 6,804,545 B2 | 10/2004 | Fuimaono et al. |
| 6,805,128 B1 | 10/2004 | Pless et al. |
| 6,805,129 B1 | 10/2004 | Pless et al. |
| 6,830,576 B2 | 12/2004 | Fleischman et al. |
| 6,840,936 B2 | 1/2005 | Sliwa, Jr. et al. |
| 6,845,257 B2 | 1/2005 | Fuimaono et al. |
| 6,858,026 B2 | 2/2005 | Sliwa et al. |
| 6,866,662 B2 | 3/2005 | Fuimaono et al. |
| 6,872,205 B2 | 3/2005 | Lesh et al. |
| 6,942,661 B2 | 9/2005 | Swanson |
| 6,971,394 B2 | 12/2005 | Sliwa, Jr. et al. |
| 6,987,996 B2 | 1/2006 | Fuimaono et al. |
| 7,011,655 B2 | 3/2006 | Thompson et al. |
| 7,013,169 B2 | 3/2006 | Bowe |
| 7,013,170 B2 | 3/2006 | Bowe |
| 7,025,766 B2 | 4/2006 | Whayne et al. |
| 7,052,493 B2 | 5/2006 | Vaska et al. |
| 7,099,711 B2 | 8/2006 | Fuimaono et al. |
| 7,123,951 B2 | 10/2006 | Fuimaono et al. |
| 7,181,262 B2 | 2/2007 | Fuimaono et al. |
| 7,187,963 B2 | 3/2007 | Coleman et al. |
| 2004/0034348 A1 | 2/2004 | Rashidi |
| 2004/0106897 A1 | 6/2004 | Thompson et al. |
| 2004/0143175 A1 | 7/2004 | Coleman et al. |
| 2005/0010095 A1 | 1/2005 | Stewart et al. |
| 2005/0187455 A1 | 8/2005 | Rashidi |
| 2005/0187456 A1 | 8/2005 | Rashidi |
| 2005/0222554 A1 | 10/2005 | Wallace et al. |
| 2006/0095022 A1 | 5/2006 | Moll et al. |
| 2006/0100610 A1 | 5/2006 | Wallace et al. |
| 2006/0184106 A1 | 8/2006 | McDaniel et al. |
| 2006/0241366 A1 | 10/2006 | Falwell et al. |
| 2007/0038055 A1 | 2/2007 | Fuimaono et al. |
| 2007/0156116 A1 | 7/2007 | Gonzalez |
| 2007/0179375 A1 | 8/2007 | Fuimaono et al. |

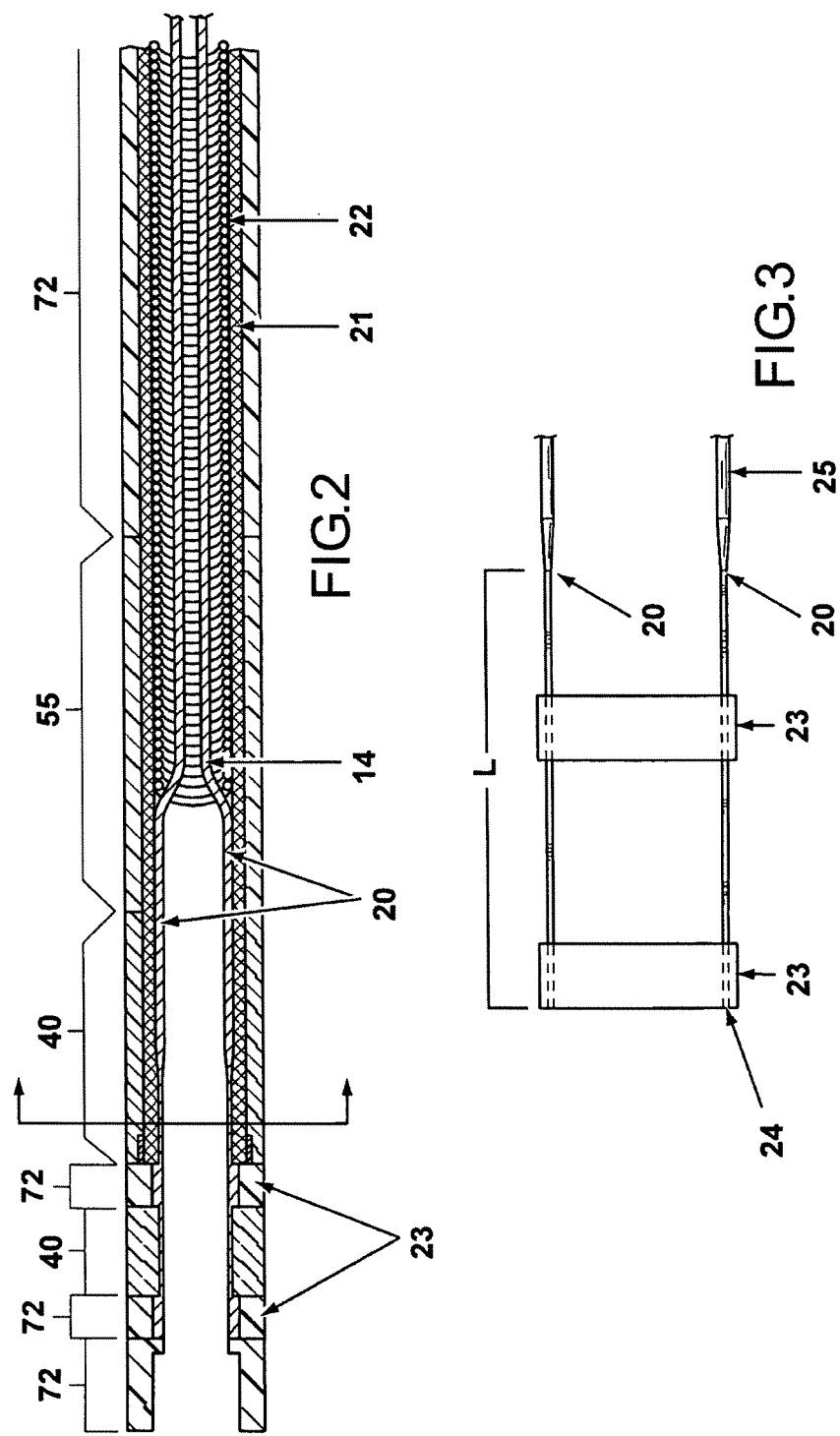

DEFLECTABLE VARIABLE RADIUS CATHETERS

CROSS-REFERENCE TO RELATED APPLICATIONS

This application is a divisional of U.S. application Ser. No. 12/569,786, filed 29 Sep. 2009, now allowed, which is a divisional of U.S. application Ser. No. 11/647,311, filed 29 Dec. 2006, now abandoned, which claims benefit of U.S. provisional application 60/800,851, filed 17 May 2006. The forgoing applications are hereby incorporated by reference as though fully set forth herein.

BACKGROUND OF THE INVENTION a. Field of the Invention

The invention relates to catheters with improved deflectable and/or control characteristics, methods of using the catheters, and methods of producing them. In one aspect, for example, the invention encompasses a catheter design that allows a desired loop or partial loop to be formed at a distal end and the loop to be further controlled, for example, by contracting or extending into a spiral form or into a variable size and length, and also to be controlled in bilateral movement left to right without the bilateral movement affecting the contracting or extending, or vice versa. Thus, the invention provides improved control over the motion of the catheter. The catheter can also replace the use of multiple catheters having different distal end loop sizes with a single, flexible catheter capable of forming variable loop sizes along its length.

b. Background Art

Deflectable or steerable catheters are used in various medical and surgical procedures, including ablation, such as arrhythmia ablation, mapping, such as cardiac mapping, and drug delivery, such as intracardial drug delivery. The steerable function can be accomplished by three modes of actions: straight translational movement along the direction of the catheter length; deflection of an end or distal section in one direction or in one plane; and turning of the catheter shaft to direct the deflected end toward the desired point. A control wire or pull wire positioned inside the catheter, usually connecting to the distal end, is used to direct the degree of deflection of the distal section. As known in the art, a catheter typically comprises a distal end that enters the body, and a proximal end that controls the movement or function at the distal end, the proximal end remaining outside the body. Deflection is generally within one plane, having only a curl or sweep profile. The control wire is operably connected to some type of a pulling mechanism, which is connected to a control device at the proximal end of the catheter shaft. The degree of pulling on the mechanism directs the movement of the control wire and thus the degree of deflection of the distal end of the catheter shaft.

In many cases, the control wire is located off of center relative to the catheter shaft. This allows a curve toward an intended deflection side. When the control wire is pulled, the catheter deflects toward the side of the catheter in which the wire is located. A bidirectional deflection is also possible, where two control wires are located on opposite sides of the catheter and the pulling on one control wire causes a deflection in one direction in a plane, and pulling on the other causes the opposite deflection in the same plane.

There are several known deficiencies with the use of existing steerable catheters. For example, the control in the direction of deflection is limited, and both the surface of the catheter and the interior space used for the control wire can operate inefficiently to cause unintended movement, or lack of movement, of the catheter tip. Furthermore, for those catheters designed to form a loop at the distal end, the size and shape of the loop is generally fixed by the length of the pull wire and/or the loop form is fixed within a single plane. Thus, catheters capable of improved control of the distal tip and those capable of forming a loop of variable sizes are desired in the art.

BRIEF SUMMARY OF THE INVENTION

It is desirable to be able to direct catheter tips or distal sections of catheters in a variety of directions to accommodate numerous surgical procedures and anatomical features. In one aspect, the invention provides a deflectable catheter capable of forming one of many variable radius, spiral forms from a flexible distal end section. In one embodiment, the catheter employs a variable radius control wire to extend, contract, or deform a pre-formed loop structure, as a loop structure is typically produced from conventional, bidirectional deflectable catheter. The extended loop can essentially create a three dimensional, spiral-like form or geometry. The loop can also form a partial or complete circle. The ability of a single catheter to create the multitude of shapes and sizes possible allows a user to access a greater number of anatomical areas without changing the catheter or the size of the distal end during a procedure or treatment.

In a general aspect, the invention provides a catheter comprising a proximal section with a shaft and a control actuator at a proximal end, where the control actuator is connected to two or more bidirectional control wires. These wires can be engaged at the proximal end to produce a left to right motion in the distal end. The proximal section also comprises a second control actuator for separate control of a variable radius control wire. A distal section of the catheter comprises, at desired points along its length, at least one electrode, such as a sensing electrode or ablation electrode, and the distal section also comprises a connection point for the variable radius control wire, and a connection point for the at least two bidirectional control wires. The connection point for the variable radius control wire is typically in the loop section, while the connection point for the bidirectional control wires is proximal to the connection point for the variable radius control wire. Of course, the engagement of the control wire or wires and the engagement of the variable radius control wire can occur simultaneously to produce two independent planes of motion. The two independent planes of motion are allowed by use of two separate compression coils, one for each plane of motion, the motion in each plane is accomplished independently of motion in the other plane, and is done without affecting the position of the distal tip in the other plane.

The first compression coil can be in the inside diameter of the polymer shaft of the catheter, and extend from the proximal end of the shaft to the distal end of the straight portion of the shaft. The two bidirectional control wires are housed inside this first compression coil. Also housed inside the first compression coil is the second compression coil. While there can be a connection of the two compression coils at the proximal end of the second compression coil, the first and second compression coils are generally not connected, and may move independently of each other in the lateral direction. The variable radius control wire is housed in the lumen of the second compression coil. The second compression coil can run from the proximal end of the catheter to the tip electrode, or can run from a point on the first compression coil to a point inside the loop.

Various alternatives and specific embodiments of this general catheter are possible. For example, the catheter can further comprise a shape wire at the distal section, where the shape wire is preferably a Nitinol composition. The radius control wire can be connected to the distal end and the distal end can comprise a tip electrode. The catheter distal section can be composed of a variety of external, biocompatible coatings or coverings as known in the art, including a flexible polyether block amide, such as one of the many Pebax polymers available. More than one polymer composition can be used along the length of the distal section and at least two polymer compositions can have different hardness properties on the durometer A scale. When two bidirectional control wires and one variable radius control wire are used, the bidirectional control wires and the variable radius control wire can be housed separately within separate compression coils. The variable radius control wire is in a separate compression coil to avoid unintended left to right movement of the distal tip section of the kind preferably controlled by the bidirectional control wires when engaging the variable radius control wire to adjust the loop at the distal end. In a preferred embodiment, additional control of the desired loop form or spiral form can be achieved by using a flattened wire portion of the variable radius control wire, such that, for example, the most distal end and the end connecting to the tip or near the tip is a flattened wire. The use of flattened wire sections enables increased control over the loop.

In another general aspect, the invention provides a method of using the catheters and distal end sections of catheters. For example, the methods can be used to form a desired three-dimensional spiral form in a catheter distal section, and for positioning the catheter in an intracardial, epicardial, or pulmonary vein area. These methods can comprise inserting the catheter into a patient and advancing the catheter end to desired position. By engaging at least one control wire, one produces a desired loop form from a desired distal end structure, comprising the control wire and pull ring features noted above or throughout this disclosure. Engaging the variable radius control wire can extend the desired loop form into spiral form. Preferably, two bidirectional control wires are used that are together capable of causing a desired loop to form in the distal section of the catheter. A preferred method of using the catheters of the invention includes use in mapping or ablating the pulmonary vein ostium and surrounding areas of the heart, as in atrial fibrillation diagnosis and treatment procedures known in the art.

In another general aspect, the invention provides a deflectable catheter comprising a flexible distal end section, having a distal tip and optionally a tip electrode, and having a proximal end with two or more actuators for controlling the shape of the distal end section. A first control wire, and optionally more than one control wire, is connected to a desired deflection point at or near the end of a straight portion of the central shaft region, and a variable radius control wire is connected at or near the distal tip or tip electrode. As commonly known, the catheter can include a central shaft region that connects the distal end section to a handle and actuator at the proximal end. The shaft includes connections or continuing wire lengths so that a first, and optional additional control wire and the variable radius control wire can be operably attached to the actuators at the proximal end for the user to engage the wires. One of the actuators at the proximal end can engage a first control wire to produce a left to right motion at the end of the straight portion of the central shaft region. Then, another actuator at the proximal end that engages the variable radius control wire can reduce or extend the radius of the loop.

In another aspect, the invention provides a deflectable shaft and deflectable loop. The deflectable loop can be composed of an outer polymeric member with attached sensing electrodes, shape wire, control wire, tubing, and tip electrode. In a preferred embodiment, the polymers used at different points or sections of the catheter can differ, so that sections at the proximal end are made of a harder composition than the sections at the distal end. More particularly, a pattern of polymers having desired hardness, such as with the Shore D or durometer D hardness scale, can be selected for a particular section of the catheter to accommodate an expected or desired curvature during the use of the catheter.

Examples and preferred methods to produce the catheters of the invention and the final selection of internal tubing, sheathing, reinforcing braids or tubes, and heat-shrinking polymers to produce a desired inside and outside diameter are noted below.

A variety of catheters can be produced or used in accordance with the disclosure of this invention, including, without limitation, steerable catheters, introducers, RF or ultrasound ablation catheters, urologic catheters, drainage catheters, coronary sinus catheters, angiography catheters, catheters for locating pulmonary veins, intra-cardiac echo catheters, aortic bypass catheters, stent delivery or balloon catheters, imaging agent or contrast agent or drug or biological agent delivery catheters, EP or cardiac mapping catheters, sizing catheters, all in a wide variety of lengths and diameters. One of skill in the art is familiar with adapting the use of a deflectable or steerable catheter in a variety medical and surgical procedures.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 2 depicts a cross sectional view of an exemplary combination of the inner control wire assembly of a catheter of the invention.

FIG. 3 is a view of the pull ring section as shown in FIG. 2.

DETAILED DESCRIPTION OF EXEMPLARY EMBODIMENTS OF THE INVENTION

Figure 1A:
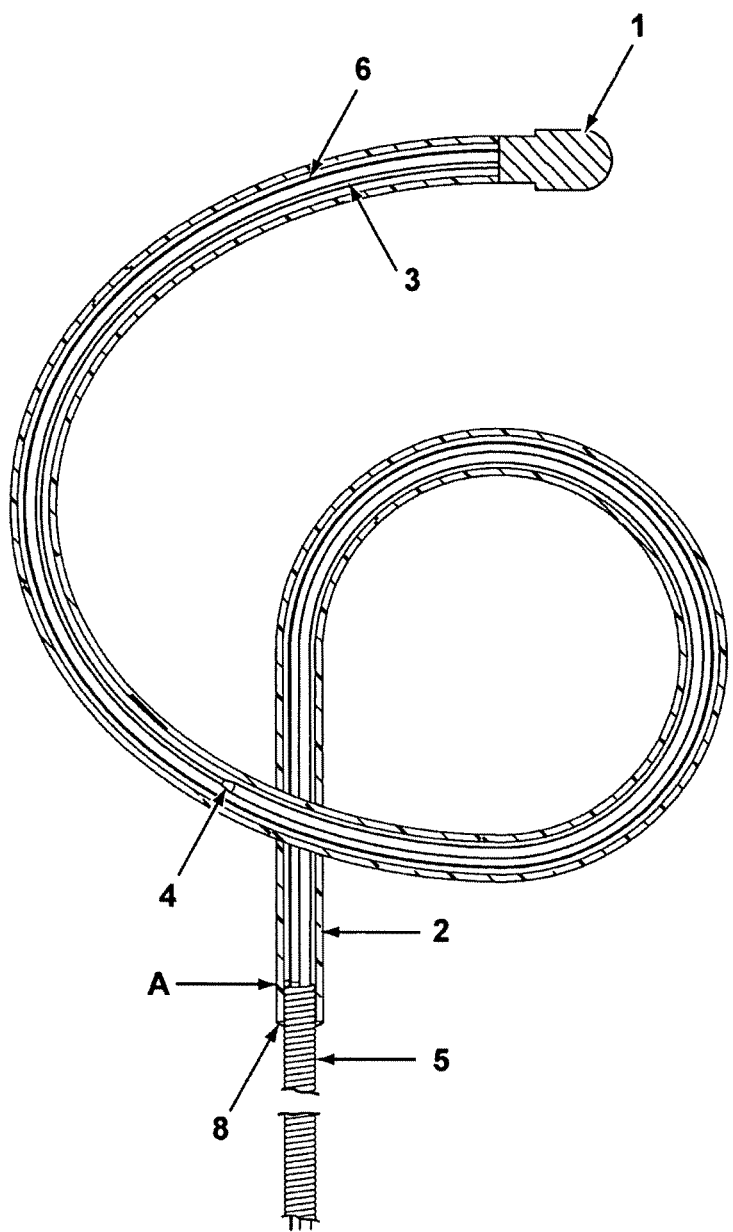
FIG. 1A depicts a distal loop assembly or distal loop section of a catheter, comprising a control wire section and tip electrode consistent with the invention. In this design, the electrode tip has a recessed distal section to allow a multiple sensor or electrode ring assembly (FIG. 1B) to fit over the length and terminate at the recessed section of the tip to produce a smooth end.

Throughout this disclosure, applicants refer to texts, patent documents, and other sources of information. Each and every cited source of information is specifically incorporated herein by reference in its entirety. Portions of these sources may be included in this document as allowed or required. However, the meaning of any term or phrase specifically defined or explained in this disclosure shall not be modified by the content of any of the sources.

The headings (such as "Brief Summary") used are intended only for general organization of topics within the disclosure of the invention and are not intended to limit the disclosure of the invention or any aspect of it. In particular, subject matter disclosed in the "Related Art" includes aspects of technology within the scope of the invention and thus may not constitute solely background art. Subject matter disclosed in the "Brief Summary" is not an exhaustive or complete disclosure of the entire scope of the invention or any particular embodiment.

As used herein, the words "preferred," "preferentially," and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention and no disclaimer of other embodiments should be inferred from the discussion of a preferred embodiment or a figure showing a preferred embodiment. In fact, the nature of the devices and methods of the invention allow one of skill in the art to make and use the invention on many medical or surgical devices available or contemplated.

In one preferred embodiment, the invention comprises a catheter and the use of a catheter that in addition to bidirectional control wires to control movement, in one direction or another at a distal end or section, also comprises a control wire or wires for varying the radius of a formed loop or over a portion of a formed loop (variable radius control wire(s)). In practice, the invention advantageously allows the user to form desired three dimensional structures, such as a spiral structure, with a distal section of a catheter. This spiral structure can be used to access a number of tissue areas and anatomical features with improved control and accuracy compared to earlier devices and methods. In one preferred aspect, the spiral structure can be used to access the interior form of one or more pulmonary veins, such as during a pulmonary vein isolation (PVI) procedure. Thus, the invention specifically allows the formation of a three-dimensional spiral structure with a section of a medical device, particularly a catheter and even more particularly a catheter used in PVI mapping or ablation procedures.

With respect to intracardial, pulmonary vein and PVI procedures in general, the invention allows a single distal loop to form variable sizes in order to avoid the problem of using two or more catheters to reach desired anatomical features or electrophysiological elements in a patient because the loop can be moved left or right without changing the shape of the loop, and the size of the loop can also be changed without moving the loop left to right. The operator has increased control over the location of the loop. Thus, in one aspect, two independent types of motion are allowed by the use of a separate the left/right movement from movement controlling the shape or size of the loop movement, and the mechanisms controlling these two types of movement can be separated into two separate compression coils. For example, a first compression coil can be in the inside diameter of the polymer shaft of the catheter, and extend from the proximal end of the shaft to the distal end of the straight portion of the shaft. The two bidirectional control wires can be housed inside this first compression coil. Also housed inside the first compression coil is a second compression coil. The first and second compression coils need not be connected at any point of the shaft and allow independent movement of the control wires housed in them. Thus, the variable radius control wire can be housed in the lumen of the second compression coil. The second compression coil can run from the proximal end of the catheter to the tip electrode, or can run from a point on the first compression coil to a point inside the loop. In the past, multiple loops or distal structures may have been required during certain procedures because of individual variations in anatomy or size.

In another general aspect, the catheter comprises a compression coil, a pull ring assembly, a reinforced member of metallic, composite, or polymeric filament, and a flexible outer layer, preferably of one or more biocompatible polymers.

A number of polymers have been suggested for use in medical device and catheter applications, including: polyethylene; polyetherimide; polypropylene; polyetheretherketone (PEEK); polytetrafluoroethylene (PTFE) or Teflon (DuPont, Wilmington, Del.); Ultra High Molecular Weight (UHMW) polyethylene; high density polyethylene (HDPE); polyimide; polyaryletherketones; polyetheretherketones; polyurethane; polypropylene; oriented polypropylene; polyethylene; crystallized polyethylene terephthalate; polyethylene terephthalate; polyester; polyoxymethylene or Delrin (DuPont, Wilmington, Del.); polyamide-imide (PAI) or TORLON (Solvay Advance Polymers, Alpharetta, Ga.);

polyoxymethylene (POM), acetal resin, or Delrin (DuPont, Wilmington, Del.); and polyvinylidene fluoride or Kynar (Atochem Corporation). One of skill in the art is familiar with selecting the appropriate polymer or polymer combinations to achieve the flexibility and lubricity properties desired. In some examples, flexible elostomers, such as polyether block amide—PEBA, such as Pebax®, a registered trademark of Atofina Chemicals, are a preferred polymer for use in the invention and methods especially for the external coating of the catheters, and especially in varying hardness according to the Durometer D or Shore D scale, known in the art.

In one embodiment, the invention comprises a deflectable shaft and a deflectable loop-forming distal section. The deflectable loop can comprise, consist, or consist essentially of an outer polymeric layer made of a 72 Durometer Pebax segment proximally and 40 Durometer Pebax segment distally. Any of the biocompatible Pebax polymers can be selected for use, but those with a hardness of 72 D, 55 D, and 40 D, are preferred. The loop section can also comprise polymers of varying hardness along its length, as depicted in the drawings. By varying the hardness along the lengths of the distal end or distal loop section, both the force required to manipulate through the actuators and the geometric structures the distal end section can eventually form can be controlled. The distal loop section can also comprise one or more electrodes or sensing electrodes along its length at desired points or intervals. The distal loop section can also comprise a shape wire composed of a shaped memory alloy, preferably NITINOL (an acronym for Nickel Titanium Naval Ordnance Laboratory). Other alloys or shaped memory alloys can be selected. In a preferred embodiment where a shaped wire is used, the shaped wire can be joined to a control wire or operably linked to a control wire, especially a flattened control wire or a flattened section of a control wire. The shaped wire, flattened control wire, and especially the combination of the flattened control wire and shaped wire enhance the control of the loop or curved form produced at the distal section. In another preferred embodiment, a PTFE or high lubricity polymer tubing or layer can surround the control wires, and/or the control wires and shaped wires. In another preferred embodiment, an FEP polymer tubing or layer can be used, and/or a polyimide polymer tubing or layer can be used. One of more layers of the polymers of tubing used can have desired imaging characteristics, so that the position, orientation, and the form of the distal loop section can be more easily visualized by one or more imaging techniques known or available in the art.

In a preferred aspect of any of the various embodiments disclosed, a distal end tip electrode is used. One of skill in the art is familiar with the selection of various electrodes for use in catheters, including, without limitation, sensing electrodes, ablation electrodes, RF delivery electrodes, ultrasound energy delivery probes, and others.

In another preferred aspect, at least one and preferably multiple sensing electrodes are mounted on the external polymer coating or tubing of the distal loop section. Each of the electrodes can be separately connected to a control and/or monitoring device, or multiple electrodes can be connected in series. The electrodes can be attached to the external surface by piercing holes, adhesive bonding, and subsequent stringing lead wires through the interior of the catheter shaft.

In any embodiment, including those where sensing electrodes are mounted on the external surface of the distal loop section, the invention optionally comprises a distal loop section having a pre-made form within the assembly, in order to direct the loop structure of form into a desired curve, loop, multiple loop, or curvilinear shape. As referred to herein, the term "loop" can be a simple curve, a multiple curve form, a compound curve form, a curvilinear form, an entire circle, a substantial part of an entire circle, or more than an entire circle. The drawings depict exemplary "loop" forms that can be produced during different aspects of the use of the catheters of the invention, but the drawings should not be taken as a limitation on the forms possible under this invention.

The tip electrode pull wire assembly is then inserted into the polymeric member from the distal end and inserted until the proximal end of the tip electrode is butted up to the polymer member.

Referring now briefly to the drawings, FIG. 1A depicts a distal loop assembly or distal loop section of a catheter, comprising a section (2) where a coil (5) and rounded control wire are positioned within the catheter, and a distal tip electrode (1) section consistent with the invention. As shown, a tip electrode is controlled by at least one variable radius control wire with a flattened distal end (3) connected to the tip electrode, the same control wire transitioning to a round section at a desired point (4). A shape wire (6), preferably made of Nitinol, can be used in conjunction with the flattened control wire section, and the flattened control wire (3) and shape wire (6) can be connected throughout the length of the shape wire for better control of the loop structure desired during use. A compression coil (5) can be used to cover the control wire and shape wire to allow better movement during use. Polymer tubes or sheaths (8), preferably FEP (polymer of tetrafluoroethylene and hexafloropropylene) and polyimide polymers, can surround the control wire and the outer covering of the assembly. In this design, a distal end of the compression coil surrounding the control wire ends at a desired point (10) in the loop of FIG. 1B and is bonded to the shaft of Pebax at about 72 durometer. In this design, the electrode tip has a recessed distal section to allow a multiple sensor or electrode ring assembly (FIG. 1B) to fit over the length and terminate at the recessed section of the tip to produce a smooth end.

Figure 1B:
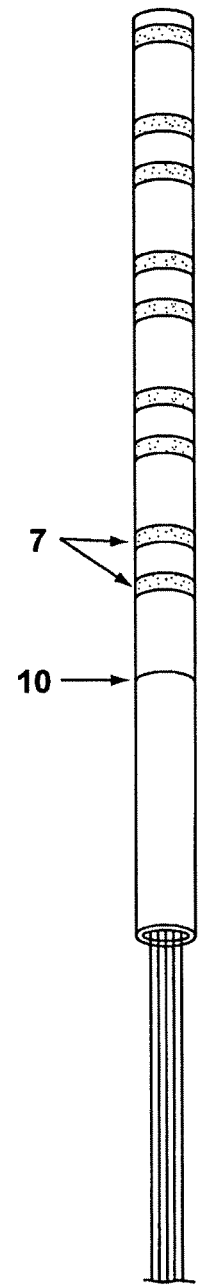
FIG. 1B depicts a multiple electrode or sensor ring assembly for use over the design of FIG. 1A.

FIG. 1B depicts a multiple electrode or sensor ring assembly for use over the design of FIG. 1A. Differing polymer compositions can be used over the length of the assembly can be used, for example to control the deflection or loop characteristics over particular sections of the catheter. The design shown in FIG. 1B includes nine ring electrodes (7) or sensors over its length, and combined with the tip electrode there is a total of ten electrodes. Other numbers of ring electrodes or sensors can also be selected, for example nineteen ring electrodes with one tip electrode.

FIG. 2 depicts a cross sectional view of an exemplary combination of the inner control wire assembly of FIG. 1A and the ring electrode assembly of FIG. 1B. The differing hardness in the ring electrode assembly is indicated by the regions (72) of 72 durometer hardness, regions (40) of 40 durometer hardness, and regions (55) of 55 durometer hardness. In this view, two control wires (20) (pull wire) are shown at 180 degrees around the radius from each other. The control wires need not be at 180 degrees or at equivalent distances from the center. A braided wire (21) area for maintaining the shape of the catheter is shown (braid) and a compression coil (22) area (coil) over a second area of the length. In this cross section, the two control wires (20) (pull wires) of the distal section are separated at a distance from the center of the shaft and are both directed to the center of the shaft at a more proximal region (14).

FIG. 3 is a view of the pull ring section as shown in FIG. 2. Each of two pull rings (23) are connected to control wires (20) (pull wires) by weld joints (24), such as laser weld joints. The area shown here is about 1.5 inches in length (L) and the area of flattened control wires encompasses this section, and can transition to a round control wire (25) after 1.5 inches.

Figure 4:
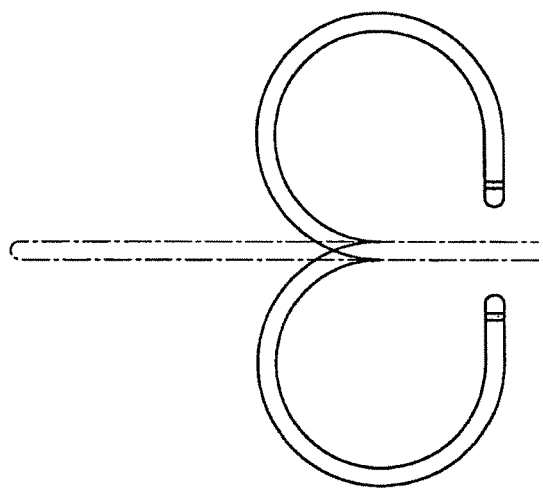
FIG. 4 depicts exemplary bidirectional deflects possible with opposing bidirectional control wires.

FIG. 4 depicts exemplary bidirectional deflects possible with opposing bidirectional control wires.

Figure 5:
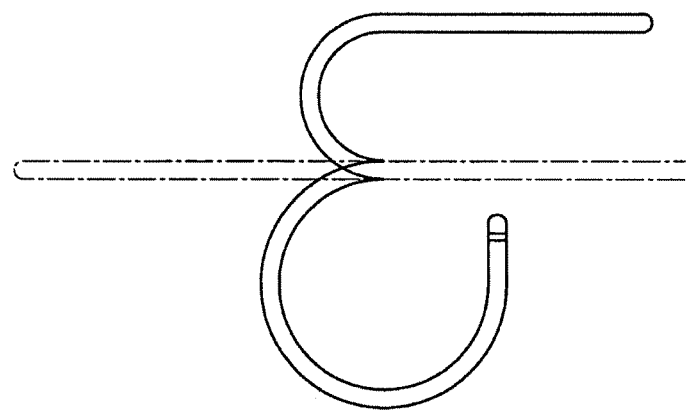
FIG. 5 depicts the various deflection forms possible using bidirectional control wires and, for example, varying the hardness of the catheter and/or varying the position of the pull rings. On the left, the control wire is attached near the distal end and the hardness is essentially uniform. On the right, the pull ring is positioned away from the most distal end, causing the curve to form at the point of the pull ring.

FIG. 5 depicts the various deflection forms possible using bidirectional control wires and, for example, varying the hardness of the catheter and/or varying the position of the pull rings. On the left, the control wire is attached near the distal end and the hardness is essentially uniform. On the right, the pull ring is positioned away from the most distal end, causing the curve to form at the point of the pull ring.

Figure 6:
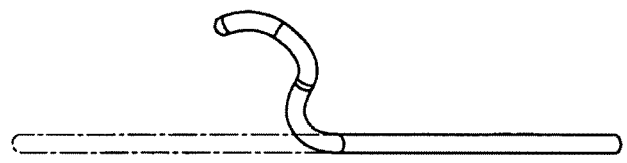
FIG. 6 depicts a multiple curve form possible by engaging two bidirectional control wires, each with a different pull ring point along the length.

FIG. 6 depicts a multiple curve form possible by engaging two bidirectional control wires, each with a different pull ring point along the length.

Figure 7A:
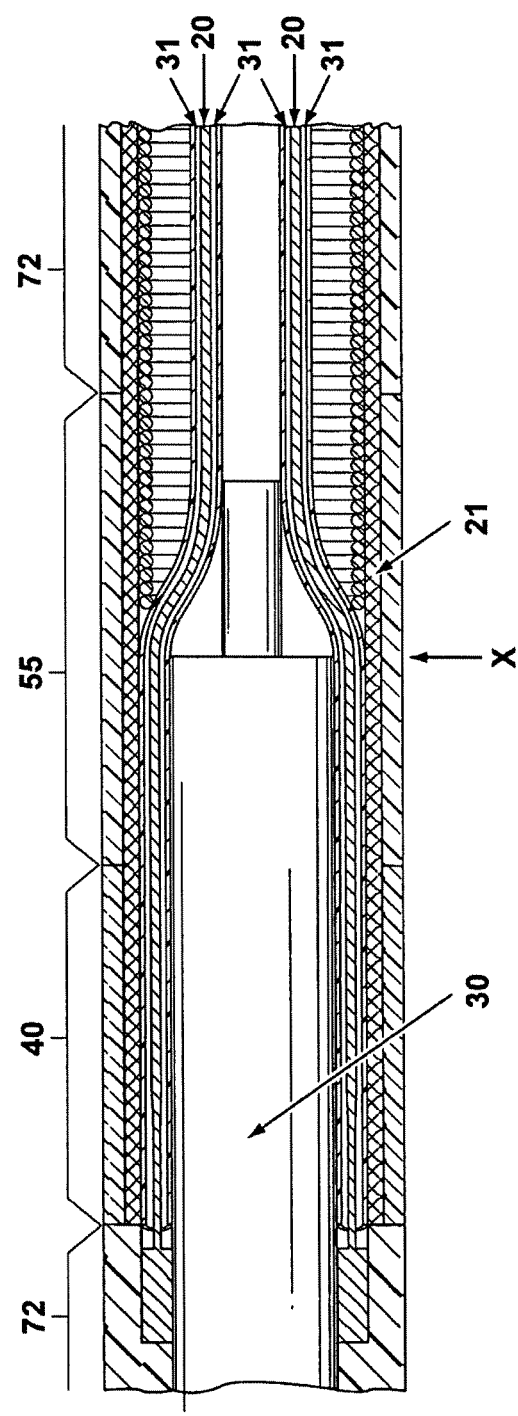
FIG. 7A depicts a catheter design during its preparation by an exemplary method. An interior mandrel is used to maintain desired diameters.

FIG. 7A depicts a catheter design during its preparation by an exemplary method. An interior mandrel (30) is used to maintain desired diameters. An exterior braid (21) maintains the structure of the exterior. A PTFE inner lining (31) can surround each control wire (20). Pebax polymers or compositions of varying hardness are shown at various sections of the exterior length (72) (40) (55) (72). A thermosetting polymer or heat shrink polymer composition (not shown) can be placed over this design with mandrel interior to compress the combined assembly into a desired diameter, then the heat shrink polymer and mandrel removed to produce the final catheter.

Figure 7B:
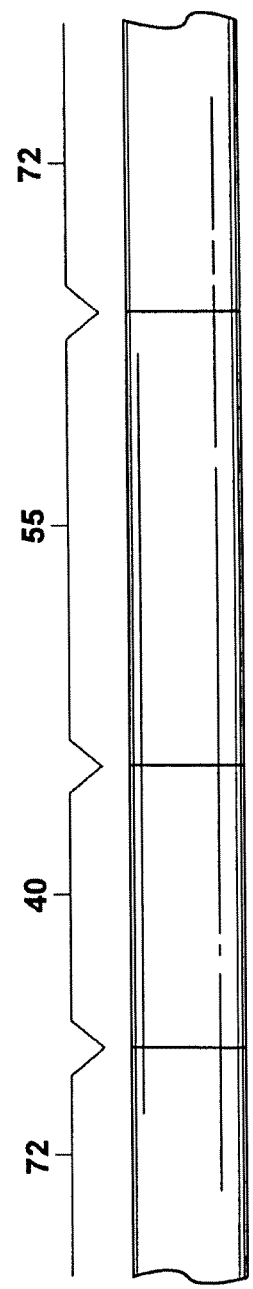
FIG. 7B depicts a similar cross sectional view as in FIG. 7A, with the top showing the sections of the shaft length and the differing polymers with differing hardness properties.

FIG. 7B depicts a similar cross sectional view as in FIG. 7A, showing the sections of the shaft length and the differing polymers with differing hardness properties.

Figure 8A:
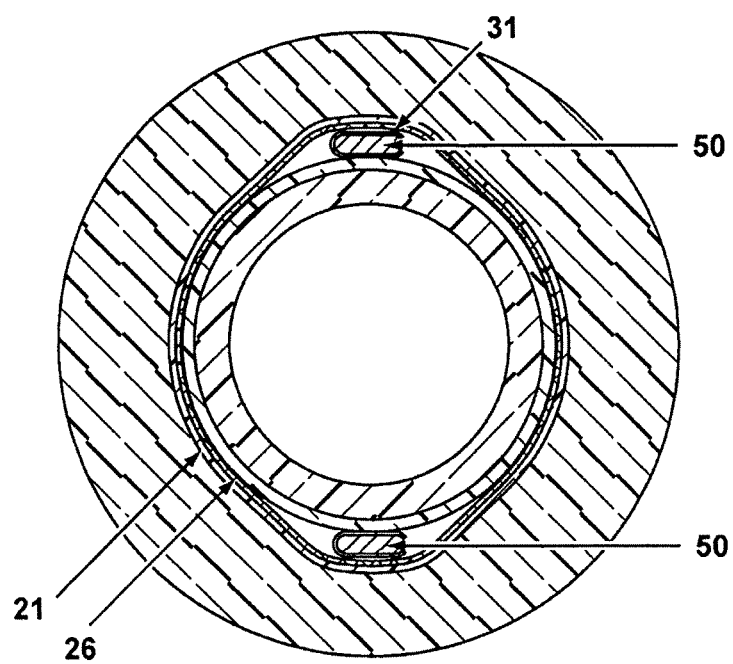
FIG. 8A is a radial cross section view of the distal area of an exemplary embodiment.
Figure 8B:
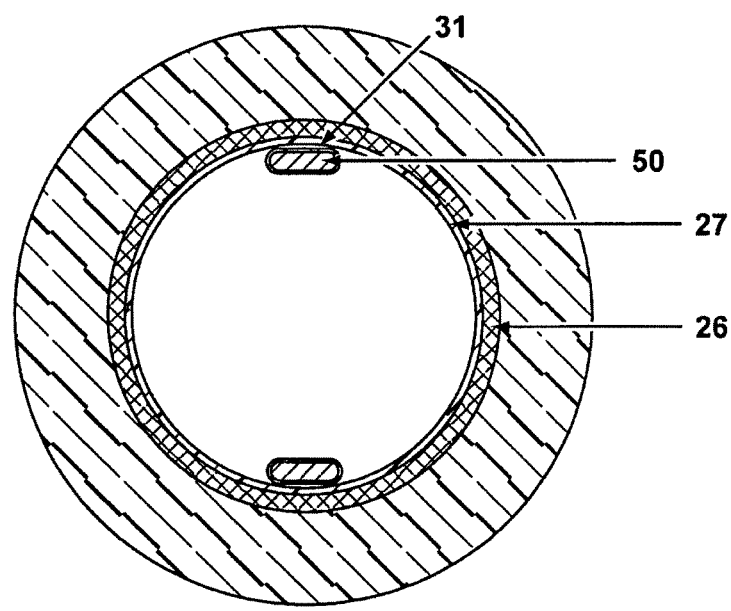
FIG. 8B is a radial cross section view of the distal area of a different exemplary embodiment.

FIGS. 8A and 8B depict alternative embodiments and layers of the cross sectional views where the flattened pull wires (50) and an optional shape wire can be located. FIG. 8A is a radial cross section view of the distal area of an exemplary embodiment showing the section where two flattened bidirectional control wires (50) are positioned 180 degrees from each other around the radius and surrounded by PTFE tubing (31) within the layers of the catheter. The different layers are shown, including braid wire (26) or reinforcing or support layer, and optional polymer layer (21), such as a shrink tube or PTFE. FIG. 8B depicts an alternative embodiment, as shown in FIG. 2, where pull wires (50) are positioned in the interior of the catheter, and inside support or braid wire (26) layer and interior polymer layer (27), such as PTFE. In FIG. 8B, polymer layer (31) surrounding pull wires (50) can also be linked or bonded to the interior layer (27) to fix the position of the pull wires, here at 180 degrees apart, but other positions are possible.

Figure 9:
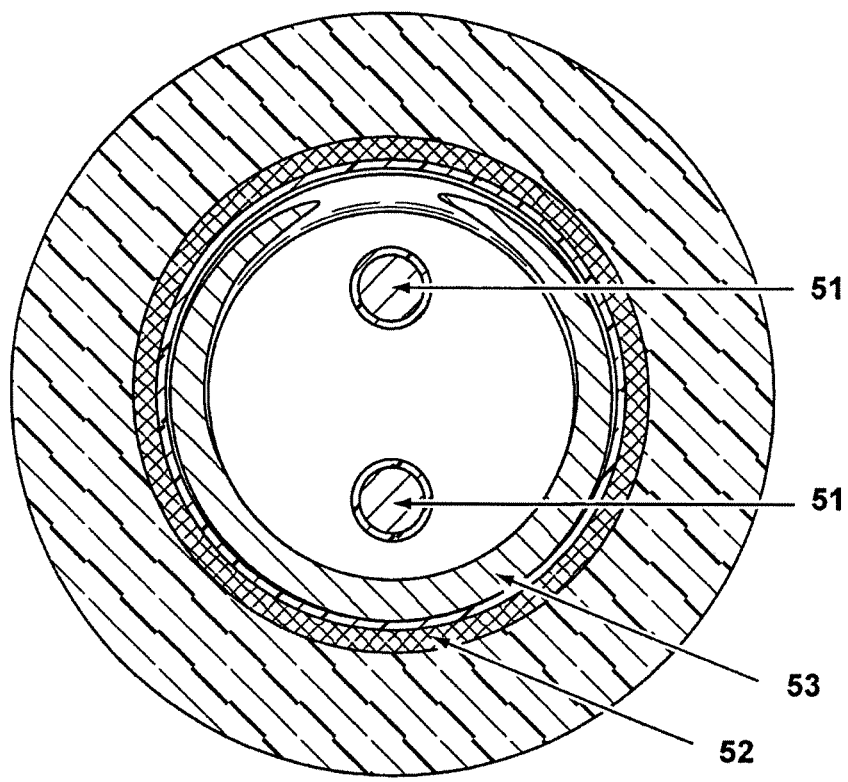
FIG. 9 shows a different radial section view at a point where the control wires are round rather than flattened.

FIG. 9 shows a different radial section view at a point where the control wires (51) are round rather than flattened. The differing thickness of the braid (52) and compression coil (53) can be selected over the length of the catheter or regions of the catheter. As depicted in these figures, different layers, including braids, compression coils, polymers, shrink tubes, and other layers, can be used at different levels within the catheter and at different combinations within the length of the catheter depending on the desired characteristics of the loop, for example. Furthermore, as noted above and shown, the position of the pull wire(s) and shape wire(s) used can be changed according to design options or manufacturing considerations.

Figure 10:
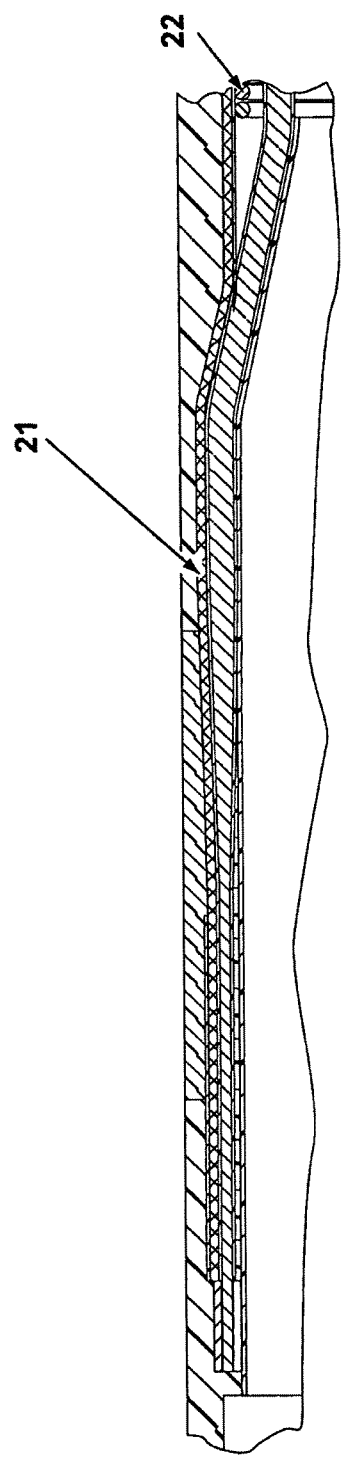
FIG. 10 shows a close-up of half of the distal section of the assembly shown in the lower part of FIG. 7B.

FIG. 10 shows a close-up of half of the distal section of the assembly shown in FIG. 7A.

Figure 11:
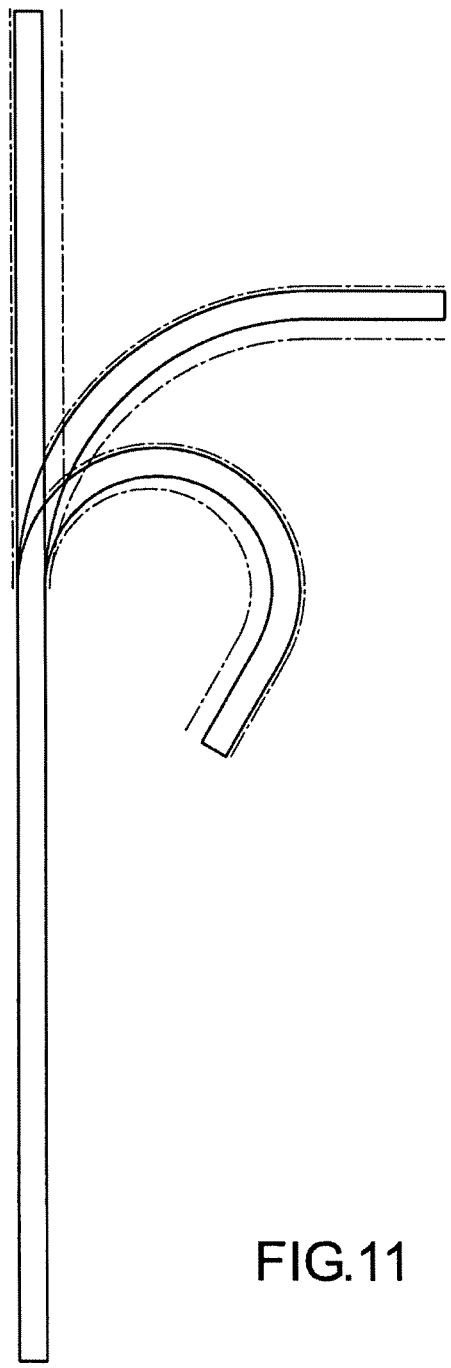
FIG. 11 shows an exemplary desired curve-shaped form at a particular deflection point.

FIG. 11 shows an exemplary desired loop formed at a particular deflection point, here a curved form.

Figure 12A:
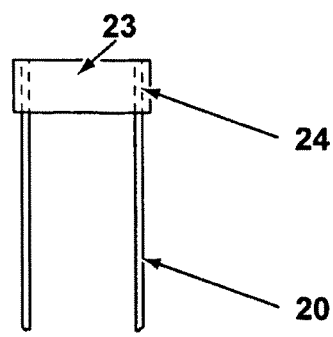
FIGS. 12A-12F show exemplary one or two pull ring designs.
Figure 12B:
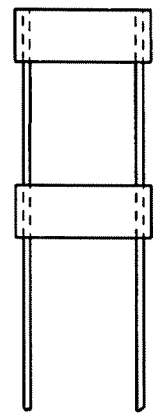
Figure 12C:
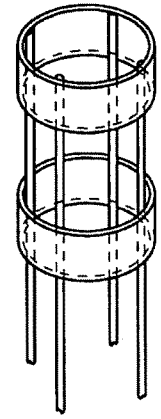
Figure 12D:
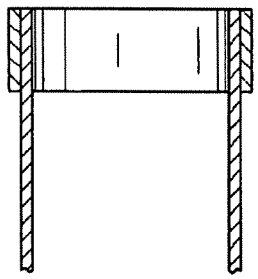
Figure 12E:
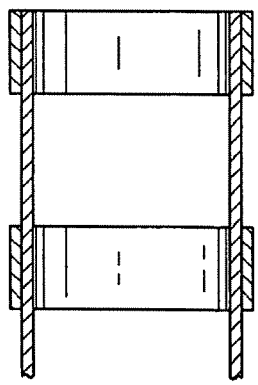
Figure 12F:
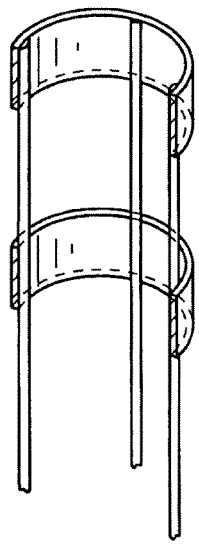

FIGS. 12A-12F show exemplary one or two pull ring (23) designs. Control or pull wires (20) can be welded (24) to the interior surface of a pull ring (23), or other surfaces including outside surface and edges of the rings. In FIG. 12C, multiple pull rings are connected to multiple control or pull wires.

Figure 13A:
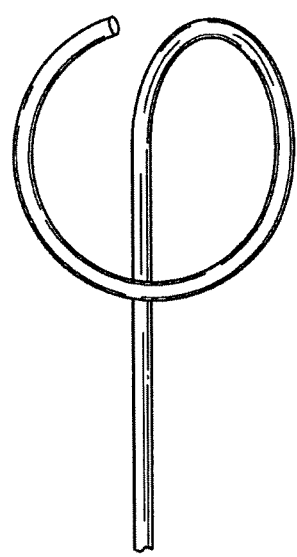
FIG. 13A depicts a loop form as in FIG. 1A.
Figure 13B:
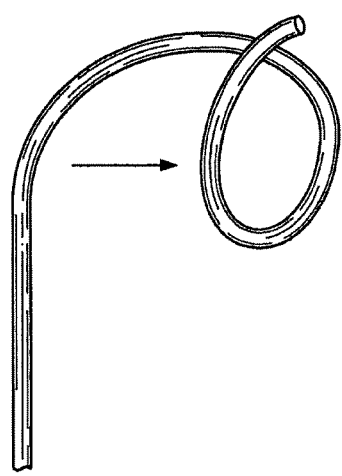
FIG. 13B depicts the effect of the variable radius control wire on a pre-formed loop structure as in FIG. 13A.

FIG. 13A depicts a loop form as in FIG. 1A. By engaging one or more bidirectional control wires or control wires, the shaft can be deflected without changing the radius or shape of the loop form. FIG. 13B depicts the effect of the variable radius control wire on a pre-formed loop structure as in FIG. 13A. The pre-formed loop essentially extends outward into a spiral form.

Figure 14A:
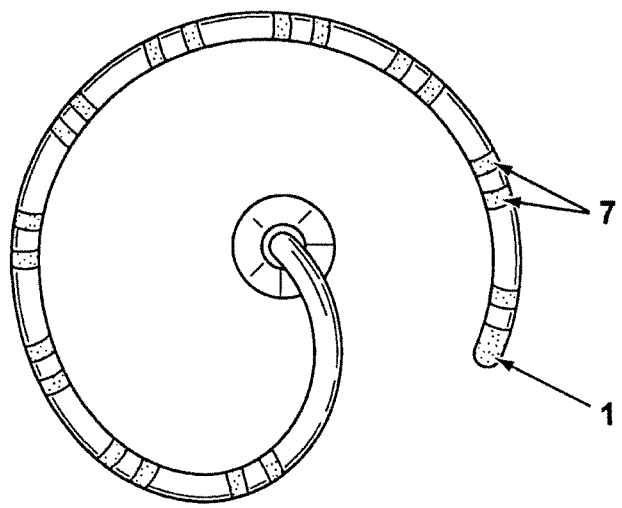
FIGS. 14A and B depict an exemplary embodiment of the distal end section with multiple electrodes on the surface and a tip electrode.
Figure 14B:
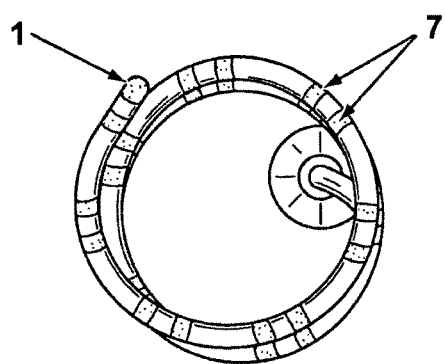
In FIG. 14B, the variable radius control wire is used to cause the loop to tighten or form a spiral with additional rotation of the tip and a smaller radius compared to the loop in FIG. 14A.

FIGS. 14A and B depict an exemplary embodiment of the distal end section with multiple electrodes (7) on the surface and a tip electrode (1). In FIG. 14B, the variable radius control wire is used to cause the loop to tighten or form a spiral with additional rotation of the tip and a smaller radius compared to the loop in FIG. 14A.

The embodiments exemplified in the drawings will now be discussed in detail as some of the many examples possible under the invention. As shown in part of the invention detailed in FIG. 1A, a distal loop assembly with a preferred flattened control wire (3), or wires, is used. A flattened control wire (3) along with a shape wire (6) can attach to the tip electrode (1), for example using a crimping method or other suitable method known in the art, such as adhesive bonding, friction fitting, chemical bonding, thermal bonding, welding (e.g., resistance, Rf, or laser welding), soldering, brazing, or any combination of these methods. In one design, a control wire can also attach to a portion of the distal loop assembly that is proximal to the tip. The control wire has a rectangular (flat) profile feature for a length of approximately 1.5 inches from the distal end. The control wire can transition to a round feature after 1.5 inches, as exemplified in FIG. 1A. The selection of the point at which a flattened control wire transitions to a round control wire can depend on the final form of a loop desired, its size, and the size, geometry, or length of a three-dimensional "loop" form desired. The use of a flattened control wire section can enhance the loop formation characteristics of the distal loop section by preventing unintended torsion build-up or release effects, such as imprecise curving, resistance to curving, or whipping of the curve or loop form during actuation of the control wires from the handle at the proximal end of the catheter. In the embodiments shown in FIGS. 1A, 1B, 7A, 8A, 8B, and 9, various polymer layers or polymer tubing can be selected for use in covering control wires and shape wires. Preferred polymers include PTFE, FEP or a polyimide. For the particular design of FIG. 1A, a bilayer FEP and polyimide tube is used to cover all of part of the shape wire and control wire. A compression coil is then slid from the proximal end of the control wire to the FEP/Polyimide tube. The compression coil and control wire are held together by either a heat shrink tube (PET or PTFE) or appropriate bond adhesive, or reflow of a polymeric tubing, e.g., Pebax. The compression coil is ideally positioned just proximal to the area in which loop or curve or compound curves are formed.

The inner or interior layer at the distal end can be constructed of polymeric material such as Polytetrafluoroethylene (PTFE), polyester, polyethylene, and similar biocompatible, flexible polymers and blends of the same. The preferred polymer material is PTFE, which provides a low coefficient of friction and high lubricity. Thermal or mechanical bonding can be used to attach the deflectable loop of FIG. 1A inside the string electrode assembly of FIG. 1B.

In methods to produce the catheters and catheter assemblies of the invention, the PTFE inner layer can be mounted on a mandrel with rectangular grooves running along the length of the mandrel and about 180 degrees apart, when the pull wires are desired at 180 degree separation. However, other configurations of the pull wires can be used. FIG. 7A shows an example of a mandrel (30) positioned inside the assembly during manufacture. Proximal to the PTFE inner layer is a compression coil, or at least one compression coil. The compression coil can be covered with heat shrink tube, preferably Polyester (PET), for structural integrity. A braided reinforcing coil or member can be positioned near the external radius of the assembly and can be constructed of a metallic material, such as stainless steel, or a polymeric or composite fiber or strand. Exemplary polymeric fibers or strands known in the art include polyester, Kevlar, Vectran, and each or a combination of them can be used as either monofilament or multifilament. One of skill in the art can select any available material for producing an appropriate braided or reinforcing member or coil to add radial stability to the assembly, and/or to prevent crimping or socking of the external layers of the catheter during use. The reinforcing member, braid or coil, can be round or flat and/or braided at different pitches and patterns, and generally extends from the proximal end to the distal end of the catheter. The particular design in FIGS. 7A, 8A, 8B, 9, and 10 can use a stainless steel wire about 0.0025 inches in diameter, but other sizes can be selected and used.

As noted above, the outer layer is constructed of polymeric material, and can be similar to the inner layer or any combination of biocompatible polymeric compositions. Polymeric material used for this external or outer layer can preferably be one or more of the Pebax polymers available, but polyethylene, polyurethane, polyester, and blends can also be selected. Pebax is used for the particular design shown in FIG. 7A, for example, and different hardness Pebax polymers can be used at desired lengths along the catheter, as shown. In one aspect of making the catheters of the invention, the final assembly is covered with a FEP shrink tube and reflowed (melt) at a predetermined temperature and time. The FEP shrink tube is then removed after reflow.

As shown in, for example, FIGS. 12A-F, the control of the deflection and loop forms possible in the distal section or assembly of the catheter during use is accomplished in part by one or more control wires. As noted above, a preferred control wire will have both a flattened or rectangular profile section and a round section, however, control wires of a variety of shapes and sizes can be selected for use. The preferred size of the control wire or wires ranges from about 0.005 to about 0.020 inches in diameter. In FIGS. 12A-F control wire attachment to one or more pull rings is detailed in various embodiments. Methods of attaching the wires to the pull rings are known in the art and include adhesives, brazing, and welding. A preferred attachment method is laser welding at the interior surface of the pull ring, and flattened section of control wires can preferably be laser welded to a pull ring. In use, the deflectable distal section or distal loop section can be articulated by pulling one or more control wires usually at an actuator in the handle section of the most proximal end of the catheter. Pulling the control wire or engaging the control wire by the actuator will cause the distal loop to deflect in a curve, as shown, for example, in FIG. 4, 5, or 11. Engaging or pulling each of two bidirectional control wires with different connection points along the distal loop section can cause the entire distal loop section to deflect in a left to right motion. With the teachings of this disclosure and the knowledge available, one of skill in the art can produce a large variety of loop or curve forms for the distal section of a catheter, and the invention is not limited to any particular loop or curve form.

For example, to accomplish various curve forms or geometries and multiple deflections, a system of pull wires and pull ring combinations can be devised. As shown in FIG. 3, the control wires can be attached to two rings one-half of an inch apart by means of laser welding, brazing, or other suitable methods known in the art. As shown in FIGS. 8A and 8B and 9, an embodiment with two control wires has a preferred configuration with the control wires positioned 180 degrees apart. The following are a few combinations of control wire and pull ring options available, but should not be taken as a limitation to the scope of forms possible.

To achieve unidirectional or bidirectional loop actuation, one ring can be attached to the pull wires. This will articulate in one or both directions with symmetrical curve profile (FIG. 4).

To achieve bidirectionality and asymmetry, two pull wires can be attached to two pull rings that are welded at different predetermined positions. Actuating one pull wire will achieve one curve profile while articulating the opposite pull wire will achieve a different curve profile (FIG. 5).

To achieve bidirectionality in different plane and curve profiles, four (4) pull wires are attached to two pull rings at a predetermined location (FIG. 6).

In another aspect of the invention, the use of multiple compression coils to isolate the movement or displacement of the various control wires can be incorporated into the design of the catheters of the invention. For example, in a preferred embodiment, a compression coil housing the variable radius control wire is separate from another compression coil housing the bidirectional control wire or wires. In a more particular embodiment, the proximal ends of both of these compression coils ends at the handle, at the proximal end, and can be joined by conventional techniques to the handle or its housing, such as adhesive bonding or UV bonding, either separately or together. The distal ends of the compression coils can end at different points along the catheter. A first compression coil can overlap a second, for example. The second compression coil can reside, to the extent it overlaps with the first, in the lumen of the first compression coil. The second compression coil can extend into the distal loop section, while the first compression coil ends proximal to that point.

In another preferred embodiment, the proximal end of the second compression coil bonds to the first compression coil, but thereafter proceed independently to the distal loop section.

A first compression coil can extend from the handle to a point in FIG. 7A (X). A second compression coil can extend from the handle to the point (A) labeled in FIG. 1A, where it is bonded to 72 D hardness polymer. When the distal tip section is prepared as a 6 F size catheter, and the shaft section represented in FIG. 7A or B is prepared as a 7 F size, the distal end section can be fitted inside the shaft section. Then, the two sections can be bonded together to form an effective connection where the action of the variable radius control wire, which traverses the length of the catheter and can optionally be used as the tip electrode lead, causes contraction or expansion only distal to end of the second compression coil. In other embodiments, the placement of the ends of the compression coils used to house the different wires can advantageously provide design options for producing geometric forms in the distal end section. As noted above, tubing, such as high lubricity or PTFE tubing, can be used to encase the control wires, or any combination of control wires, to improve the displacement or engagement of the wires. The PTFE tubing can also be used as the inner most layer of the catheter, over the length or in specific regions.

The use of the catheter to form a three dimensional, variable radius and/or three dimensional or spiral form from any of the curve or loops forms noted here or possible with one or more control wires can be achieved, in one aspect, by providing a variable radius control wire. The variable radius control wire in essence exerts a force, such as pushing or pulling force, on one or more desired points on the distal section. In one alternative, the variable radius control wire exerts a pushing force from one proximal connection point on the distal section to a second distal connection point. Alternatively, the variable radius control wire exerts a pushing force simply at the distal end or one connection point at or near the distal end of the catheter and/or at the distal tip. Since the distal end has been locked into a curve or loop form by engaging the one or more control wires (such as engaging one or both of two bidirectional control wires), the pushing force causes the curve or loop to extend in another plane or dimension to essentially form a spiral or a form with spiral attributes. As used herein, the three dimensional spiral form or more generally "spiral form" refers to the result of the pushing force on a distal section of a pre-formed loop form of the distal section of a catheter. While a spiral generated from exerting a distal end section (or distal end) pushing force is preferably formed from a loop form as shown in FIG. 1A, for example, other starting curve or loop forms can be used. Where a loop as in FIG. 1A is the pre-formed loop, one of skill in the art can see the advantages of extending the loop into a third dimension, wherein the effective radius of the external surface of the distal section is smallest at the distal tip and larger as one moves proximal along the length.

The images of FIG. 14 depict alternative embodiments where the variable radius control wire can be used to tighten or modify a pre-formed curl, curve, or loop. As shown in FIG. 14A, an initial loop of approximately 360 degrees can be formed at the distal end of the catheter. Engaging the variable radius control wire through the proximal end handle or actuator essentially reduces the radius of the form and produces a spiral having an overlap for an additional 300 degrees rotation (FIG. 14B). In this embodiment, the variable radius control wire can exert a pulling force on the distal end to produce a tighter spiral form capable of entering or contacting additional anatomical areas. In an exemplary use, the catheter is inserted into the patient in a manner known in the art. An operator manipulates one or more actuators on a handle, which causes one or both of the bidirectional control wires to be displaced and the distal end deflects toward a desired anatomical area. The operator can deflect the distal end in a variety of manners depending on how the actuators are designed and the shapes desired. The displacement or engagement of one or more bidirectional control wires can then cause the distal end to form essentially any curvilinear shape, such as a loop, a spiral, or an 's' shape. As noted above, the distal end may be designed to form a desired shape using shape wires and/or variable hardness polymer compositions along its length. During engagement or after engagement to form any curvilinear shape, including a curve, loop, spiral, or an 's' shape, the engagement or displacement of one or more variable radius control wires can bring about an expansion or contraction of the curvilinear shape.

In FIG. 14B the loop is contracted into a smaller radius or a tighter spiral. Thus, in one aspect, first and second bidirectional control wires can cause a deflection in a first plane, and the one or more variable radius control wires can cause a deflection in a second plane, such as a plane perpendicular to the first plane. Of course, the use of shape wires, the connection points of pull rings, variable polymer compositions, and combinations of these and other techniques known in the art can cause the second plane to be essentially any orientation with respect to the first plane.

As shown in FIG. 13A, a pre-formed loop can be generated by one control wire, or be shape-dictated by the shape wire, and more complex or compound loops or forms are obviously possible using two control wires, or more than two control wires.

The following are some examples of the preferred aspects of the invention.

Illustrative Examples

In a pulmonary vein isolation procedure (PVI), a common step is mapping the electrophysiological characteristics using one or more sensing electrodes. The mapping procedure, as known in the art, combines positioning information through an imaging technique and electrical response information from electrodes. By providing a variable radius catheter, the mapping procedure can employ a single catheter that can vary its size and access points at or near the pulmonary veins, and at and through the pulmonary ostium, to produce a more precise map of the electrophysiology. For catheter ablation of atrial fibrillation (AF), a proper catheter positioning can be crucial to a successful treatment, and such success depends on knowledge of pulmonary vein (PV) anatomy and electrophysiology. By efficiently providing a single catheter to assess PV spatial orientation, ostial shape, and electrophysiology, the AF procedure is simplified and shortened.

The catheter of the invention with two bidirectional control wires for controlling movement of a distal loop section and with one variable radius control wire for further controlling, tightening, or extending a pre-formed structure in a third direction, for example, is used. The catheter is fed up the femoral vein, into the right atrium, introduced transseptally into the left atrium, and at least one bidirectional control wire is engaged to deflect the distal section in a desired direction. Mapping from the electrodes on the external surface of the catheter can begin at this point. To contact or record electrophysiology characteristics at points inside the pulmonary vein ostium, the loop can be adjusted to the desired size by engaging the variable radius control wire to a desired extent. A smaller radius and most distal end of the spiral, formed by engaging the variable radius control wire, can then be inserted into one or more pulmonary ostium to record electrical activity within the vein, which then can be used for mapping ostial ablation points. An ablation catheter having similar spiral form-generating mechanisms as discussed here can then be used to access and ablate the same ostial tissue, or a combined mapping and ablation catheter can be designed and used.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counter-clockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims. The invention is not limited to any particular embodiment or example given here. Instead, one of skill in the art can use the information and concepts described to devise many other embodiments beyond those given specifically here.

What is claimed is:

1. A catheter, comprising:
   a handle operatively coupled to an elongate shaft, the elongate shaft having a deflectable portion configured for steering the catheter;
   a deflectable loop extending distally of the deflectable portion, the deflectable loop including a plurality of electrodes;
   a first compression coil disposed within the catheter, the first compression coil extending along a first region of the catheter to a first location within the deflectable portion of the elongate shaft;
   a second compression coil disposed within the catheter, the second compression coil extending longitudinally along a second region of the catheter to a second location distally of the first location, wherein a proximal end of the second compression coil abuts a distal end of the first compression coil and the second compression coil extends distally into the distal loop;
   a polymeric layer surrounding at least the distal end of the first compression coil and the proximal end of the second compression coil, thereby bonding the first compression coil to the second compression coil;
   at least one control member configured for steering the deflectable portion of the elongate shaft; and
   a loop control member configured for adjusting a radius of the deflectable loop.

2. The catheter of claim 1, wherein the deflectable loop and the elongate shaft each comprise a polymeric material and wherein a hardness of the elongate shaft is greater than a hardness of the deflectable loop.

3. The catheter of claim 1, wherein the deflectable loop is biased into a loop.

4. The catheter of claim 3, wherein the loop control member comprises a loop control wire having a proximal region and a distal region, wherein the distal region of the loop control wire comprises a rectangular profile.

5. The catheter of claim 4, wherein the proximal region of the loop control wire comprises a round profile.

6. The catheter of claim 1, wherein the handle comprises at least one actuator, and wherein engagement of the actuator adjusts the radius of the deflectable loop.

7. The catheter of claim 1, wherein the deflectable loop forms a spiral.

8. The catheter of claim 1, further comprising a shape wire disposed within the deflectable loop portion.

9. A catheter, comprising:
   a handle operatively coupled to an elongate shaft, the elongate shaft having a deflectable portion configured for steering the catheter;
   a deflectable loop extending distally of the deflectable portion, the deflectable loop including a plurality of electrodes;
   a first compression coil disposed within the catheter, the first compression coil extending along a first region of the catheter to a first location within the deflectable portion of the elongate shaft;
   a second compression coil disposed within the catheter, the second compression coil extending longitudinally along a second region of the catheter to a second location within the deflectable loop, wherein a proximal end of the second compression coil abuts a distal end of the first compression coil and the second compression coil extends distally into the deflectable loop;
   a polymeric layer surrounding at least the distal end of the first compression coil and the proximal end of the second compression coil, thereby bonding the first compression coil to the second compression coil;
   at least one control member configured for steering the deflectable portion; and
   a loop control member configured for adjusting a radius of the deflectable loop.

10. The catheter of claim 9, wherein the deflectable loop and the elongate shaft each comprise a polymeric material and wherein a hardness of the elongate shaft is greater than a hardness of the deflectable loop.

11. The catheter of claim 9, wherein the deflectable loop is biased into a loop.

12. The catheter of claim 11, wherein the loop control member comprises a loop control wire having a proximal region and a distal region, wherein the distal region of the loop control wire comprises a rectangular profile.

13. The catheter of claim 12, wherein the proximal region of the loop control wire comprises a round profile.

14. The catheter of claim 9, wherein the handle comprises at least one actuator, and wherein engagement of the actuator adjusts the radius of the deflectable loop.

15. The catheter of claim 9 wherein the deflectable loop forms a spiral.

16. The catheter of claim 9, further comprising a shape wire disposed within the deflectable loop portion.

17. A catheter, comprising:
   a handle operatively coupled to an elongate shaft, the elongate shaft having a deflectable portion configured for steering the catheter;
   a deflectable loop extending distally of the deflectable portion, the deflectable loop including a plurality of electrodes;
   a first compression coil extending longitudinally along a first region of the catheter from the handle to a first location within the deflectable portion of the elongate shaft;
   a second compression coil abutting the first compression coil, the second compression coil extending longitudinally along a second region of the catheter to a second location within the deflectable loop portion;

a polymeric layer surrounding at least the distal end of the first compression coil and the proximal end of the second compression coil, thereby bonding the first compression coil to the second compression coil;

at least one control wire configured for steering the deflectable portion; and a loop control wire configured for adjusting a radius of the deflectable loop.

* * * * *